(12) United States Patent
Lee

(10) Patent No.: US 10,340,652 B2
(45) Date of Patent: Jul. 2, 2019

(54) LASER DEVICE AND METHOD FOR DRIVING LASER DEVICE

(71) Applicant: LUTRONIC CORPORATION, Goyang (KR)

(72) Inventor: Hee Chul Lee, Goyang (KR)

(73) Assignee: LUTRONIC CORPORATION, Goyang (KR)

( * ) Notice: Subject to any disclaimer, the term of this patent is extended or adjusted under 35 U.S.C. 154(b) by 0 days.

(21) Appl. No.: 15/570,623

(22) PCT Filed: May 2, 2016

(86) PCT No.: PCT/KR2016/004590
§ 371 (c)(1),
(2) Date: Oct. 30, 2017

(87) PCT Pub. No.: WO2016/175629
PCT Pub. Date: Nov. 3, 2016

(65) Prior Publication Data
US 2018/0280086 A1    Oct. 4, 2018

(30) Foreign Application Priority Data

Apr. 30, 2015 (KR) ........................ 10-2015-0061644

(51) Int. Cl.
*H01S 3/20* (2006.01)
*H01S 3/0947* (2006.01)
*H01S 3/213* (2006.01)
*H01S 3/094* (2006.01)
(Continued)

(52) U.S. Cl.
CPC .......... *H01S 3/0947* (2013.01); *A61B 18/203* (2013.01); *H01S 3/08* (2013.01);
(Continued)

(58) Field of Classification Search
CPC .. H01S 3/094076; H01S 3/1024; H01S 3/109; H01S 3/1608; H01S 3/1611;
(Continued)

(56) References Cited

U.S. PATENT DOCUMENTS 5,144,630 A * 9/1992 Lin ....................... G02F 1/3532
                                                   359/330
2003/0105456 A1* 6/2003 Lin ......................... A61F 9/008
                                                     606/5
(Continued)

FOREIGN PATENT DOCUMENTS

KR    10-0523789 B1    10/2005
KR    10-0884512 B1    2/2009
(Continued)

OTHER PUBLICATIONS

International Search Report for PCT/KR2016/004590 filed on May 2, 2016.

*Primary Examiner* — Kinam Park

(57) ABSTRACT

A laser device according to the present invention may comprise: a pumping laser supply unit for emitting a pumping laser having a nano-second pulse width; and a laser output unit disposed at one side of the pumping laser supply unit and generating an output laser which is pumped by the pumping laser to have a nano-second pulse width corresponding to the pulse width of the pumping laser.

15 Claims, 7 Drawing Sheets

(51) Int. Cl.
  *H01S 3/092* (2006.01)
  *H01S 3/16* (2006.01)
  *H01S 3/08* (2006.01)
  *H01S 3/105* (2006.01)
  *H01S 3/102* (2006.01)
  *H01S 3/109* (2006.01)
  *A61B 18/20* (2006.01)
  *H01S 3/106* (2006.01)
  *A61B 18/00* (2006.01)

(52) U.S. Cl.
  CPC ............. *H01S 3/092* (2013.01); *H01S 3/094* (2013.01); *H01S 3/094034* (2013.01); *H01S 3/094076* (2013.01); *H01S 3/105* (2013.01); *H01S 3/109* (2013.01); *H01S 3/1024* (2013.01); *H01S 3/16* (2013.01); *H01S 3/168* (2013.01); *H01S 3/1608* (2013.01); *H01S 3/1611* (2013.01); *H01S 3/1643* (2013.01); *H01S 3/213* (2013.01); *A61B 2018/00452* (2013.01); *H01S 3/1063* (2013.01)

(58) Field of Classification Search
  CPC ............. H01S 3/1643; H01S 3/1092; H01S 3/094034; H01S 3/0947; H01S 3/168; H01S 3/213; H01S 3/1063
  See application file for complete search history.

(56) References Cited

U.S. PATENT DOCUMENTS

| | | | |
|---|---|---|---|
| 2007/0237190 A1 | 10/2007 | Yoshikawa et al. | |
| 2008/0247425 A1 | 10/2008 | Welford | |
| 2012/0120979 A1* | 5/2012 | Lee | H01S 3/1026 372/53 |
| 2012/0250719 A1* | 10/2012 | Hodgson | H01S 3/042 372/70 |
| 2012/0253333 A1* | 10/2012 | Garden | A61B 18/203 606/9 |
| 2013/0043392 A1* | 2/2013 | Mildren | H01S 3/30 250/341.1 |
| 2013/0252000 A1* | 9/2013 | Takiff | C07F 5/022 428/412 |
| 2014/0321484 A1* | 10/2014 | Sierra | H01S 3/08018 372/18 |
| 2015/0306418 A1* | 10/2015 | Lee | A61N 5/0616 607/89 |

FOREIGN PATENT DOCUMENTS

| | | |
|---|---|---|
| KR | 10-2011-0003628 A | 1/2011 |
| WO | WO 98/41177 A1 | 9/1998 |
| WO | WO 2014/145707 A2 | 9/2014 |

\* cited by examiner

LASER DEVICE AND METHOD FOR DRIVING LASER DEVICE

CROSS REFERENCE PARAGRAPH

This application is a U.S. National Stage of PCT/KR2016/004590, filed May 2, 2016, which claims the priority benefit of Korean Patent Application No. 10-2015-0061644, filed on Apr. 30, 2015 in the Korean Intellectual Property Office, the disclosures of which are incorporated herein by reference.

TECHNICAL FIELD

The present invention relates to a laser apparatus and laser driving method and, more particularly, to a laser apparatus and laser driving method, which can output a laser having a nano-second pulse width and a specific wavelength.

BACKGROUND ART

A technology for treating the human body using a method of modifying the state of a human tissue or removing a specific tissue using a laser has been widely applied. A treatment apparatus for treating a variety of types of human body tissues including the skin has been actively developed using various light sources, such as a laser source, a flash lamp and an LED.

A laser apparatus outputs a laser beam having monochromatic, coherence and collimation. The laser beam output by the laser apparatus is output with energy having a different wavelength or different pulse width depending on a change in the oscillating condition of the laser beam. In general, a laser treatment apparatus that is now commercially sold outputs a laser having a pulse width of a micro-second band. For precise treatment, there is a need for the commercialization of a laser having a nano-second pulse width, but it is difficult to commercialize a laser depending on the type or wavelength of a laser medium. In particular, Er:YAG is widely used as a medical laser medium, but had a difficulty in generating a laser having a nano-second pulse width due to medium characteristics.

DISCLOSURE

Technical Problem

The present invention is for solving the aforementioned problems, and an object of the present invention is to provide a laser apparatus and method of driving a laser apparatus, which can output a laser for treatment having a nano-second pulse width.

Technical Solution

A laser apparatus according to the present invention may include a pumping laser supply unit emitting a pumping laser having a nano-second pulse width and a laser output unit disposed on one side of the pumping laser supply unit and generating an output laser pumped by the pumping laser to have a nano-second pulse width corresponding to the pulse width of the pumping laser.

Furthermore, the laser output unit may include an output laser medium absorbing the pumping laser and generating the output laser having a wavelength different from a wavelength of the pumping laser.

Furthermore, the output laser medium may include Er:YAG.

Furthermore, the laser output unit may include a total reflection mirror disposed on one side of the output laser medium, transmitting the pumping laser toward the output laser medium, and reflecting the output laser oscillated by the output laser medium and an output mirror disposed opposite the total reflection mirror on the other side of the output laser medium and partially reflecting or transmitting the output laser oscillated by the output laser medium.

Furthermore, the pumping laser supplied to the laser output unit may have a wavelength of 650 nm.

Furthermore, the output laser emitted by the laser output unit may have a wavelength of 2940 nm, and the pumping laser supply unit may include a dye laser source generating the pumping laser.

Furthermore, the pumping laser supply unit may further include a laser oscillation unit configured to emit an oscillation laser having a nano-second pulse width. The dye laser source may generate the pumping laser amplified by the oscillation laser emitted by the laser oscillation unit.

Furthermore, the laser oscillation unit may include a laser medium for oscillation absorbing externally incident light and outputting the oscillation laser. The laser medium for oscillation may include Nd:YAG.

In this case, the oscillation laser may have a 532 nm wavelength.

Furthermore, a filter unit disposed within the laser output unit, reflecting the pumping laser and transmitting the output laser may be further included.

A method of driving a laser apparatus according to the present invention may include the steps of emitting a pumping laser having a nano-second pulse width and generating an output laser pumped by the pumping laser to have a nano-second pulse width corresponding to the pulse width of the pumping laser.

Furthermore, the step of emitting the pumping laser having the nano-second pulse width may include the step of generating, by a dye laser source using a laser dye as a medium, the pumping laser.

Furthermore, the step of emitting, by a laser oscillation unit, an oscillation laser having a nano-second pulse width prior to the step of generating, by the dye laser source, the pumping laser is further included. The dye laser source may generate the pumping laser amplified by the oscillation laser emitted by the laser oscillation unit.

Furthermore, the output laser, the pumping laser and the oscillation laser may have respective nano-second pulse widths and wavelengths of 2940 nm, 650 nm and 532 nm, respectively.

Furthermore, the laser output unit and the laser oscillation unit may use media including Er:YAG and Nd:YAG, respectively.

Detailed contents of other embodiments are included in the detailed description and drawings.

Advantageous Effects

In accordance with the present invention, there is an advantage in that a laser apparatus outputting a laser of a nano-second pulse width can be configured in a compact structure.

In particular, there is an advantage in that new treatment using an Er:YAG laser is possible in accordance with the present invention because the Er:YAG laser that was difficult to output a laser of a nano-second pulse width conventionally can easily output a shot pulse laser.

MODE FOR INVENTION

Hereinafter, a laser apparatus and method of driving a laser apparatus according to embodiments of the present invention are described in detail with reference to the accompanying drawings. However, terms or words disclosed in the followings of the present embodiment should not be construed as having common or dictionary meanings, but should be construed as having meanings and concepts that comply with the technological spirit of the present invention based on the principle that an inventor may appropriately define the concept of a term in order to describe his or her invention in the best manner.

Accordingly, elements shown in the embodiments and drawings described in this specification are only the most preferred embodiments of the present invention and do not fully represent the technological spirit of the present invention. Accordingly, it would be understood that a variety of equivalents and modifications which may substitute the embodiments at the time of filing of this application may be present.

Figure 1:
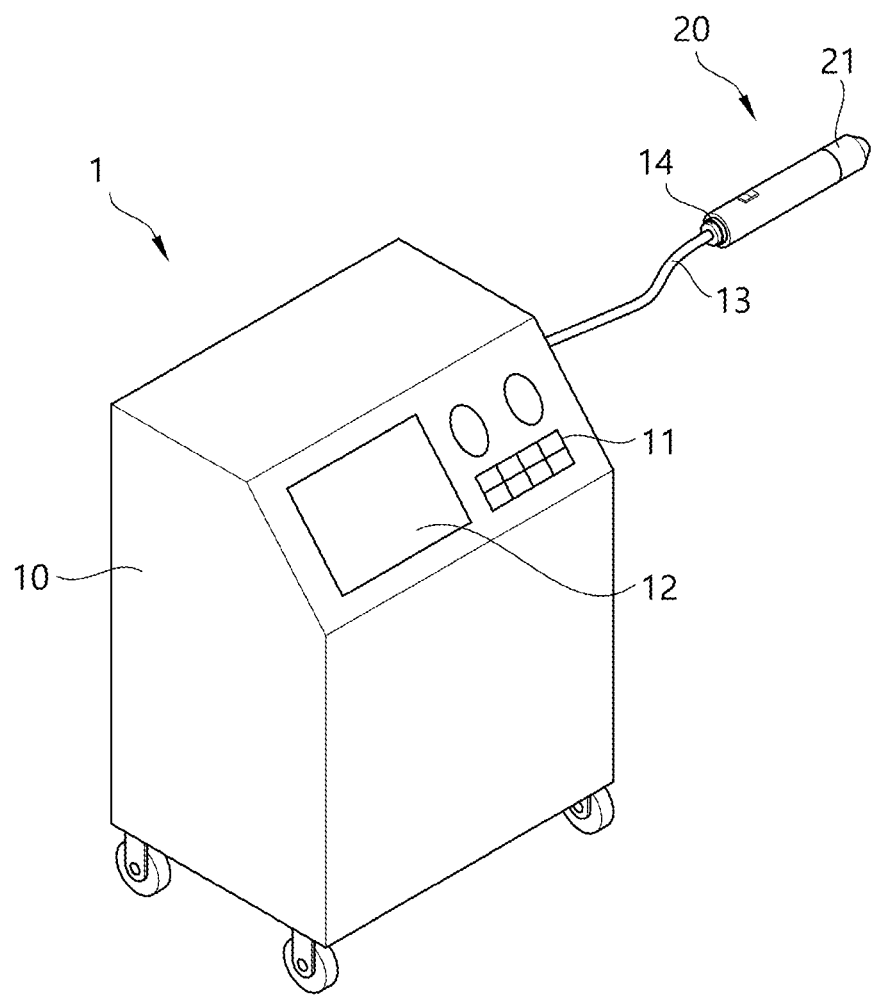
FIG. 1 is a perspective view showing a laser apparatus according to a preferred embodiment of the present invention.
Figure 2:
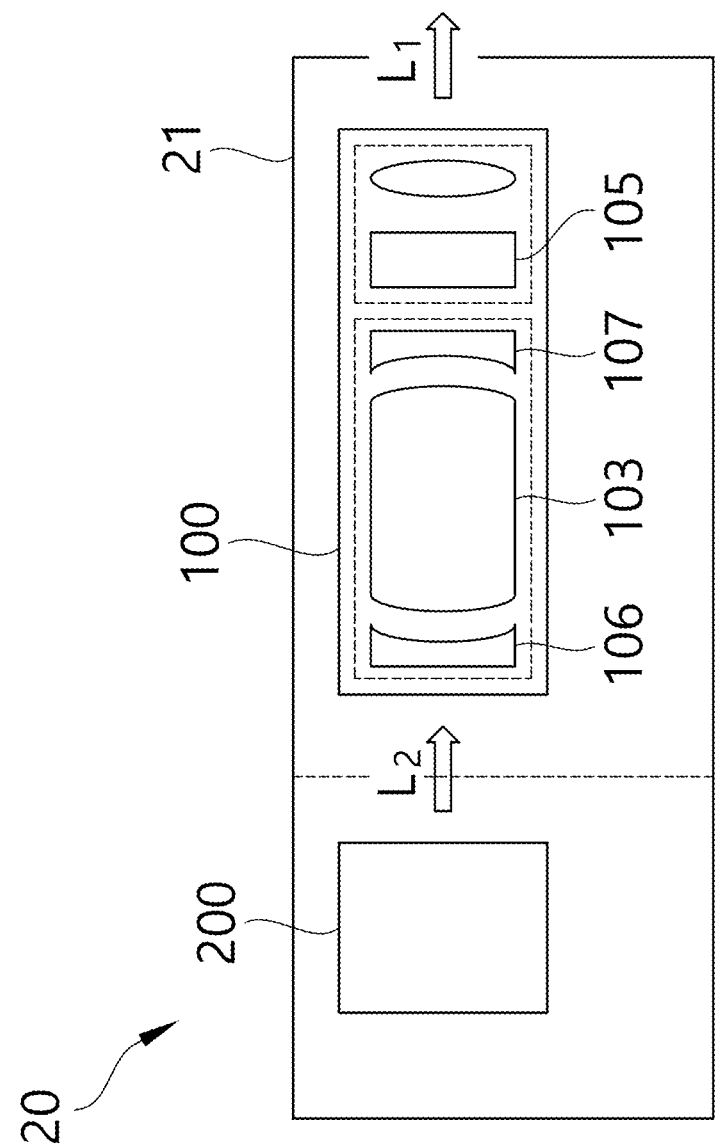
FIGS. 2 and 3 are schematic diagrams shown based on an element that belongs to the elements of the laser apparatus of FIG. 1 and that generates a laser.
Figure 3:
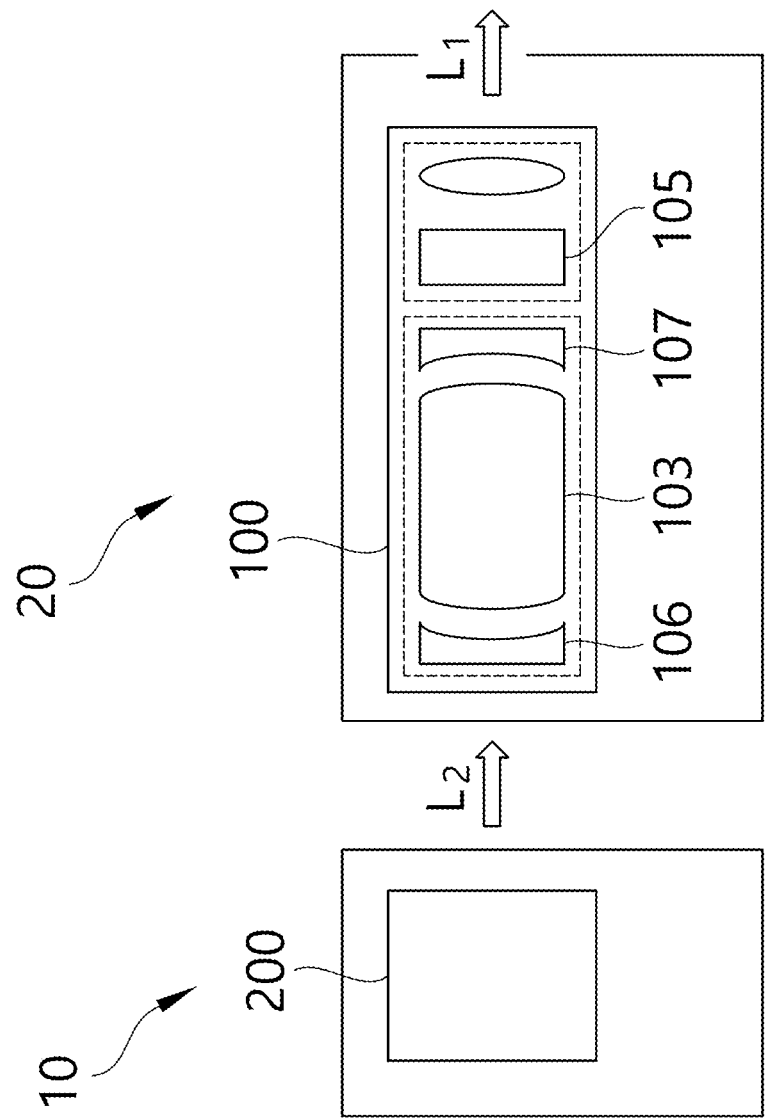

FIG. 1 is a perspective view showing a laser apparatus according to a preferred embodiment of the present invention. FIGS. 2 and 3 are block diagrams of laser apparatuses according to different embodiments of the present invention.

As shown in FIGS. 1 to 3, the laser apparatus according to the present embodiment is configured to include a main body 10, a laser radiation unit 20, a pumping laser supply unit 200 and a laser output unit 100. The laser apparatus 1 according to an embodiment of the present invention may be used in various industrial fields using a laser of a wavelength band output by the laser apparatus 1 of the present invention in addition to various medical industrial fields, such as a field for skin treatment.

A variety of types of elements generating a laser using externally supplied power may be disposed in the main body 10. A control panel 11 for manipulating the driving contents of the laser apparatus 1 and a display 12 for displaying manipulation menus and operating contents to a user may be disposed in the external surface of the main body 10.

Furthermore, a cable 13 is extended and disposed on one side of the main body 10. The laser radiation unit 20, such as a hand piece, may be connected to a clamping unit 14 at the end of the cable 13. The clamping unit 14 of the cable 13 may be disposed to be connected to the end of the laser radiation unit 20 by screw coupling and may be configured in various coupling manners.

Meanwhile, the laser radiation unit 20 is connected to the cable 13 of the main body 10, and thus a laser generated by the main body 10 is transferred to the laser radiation unit 20. The laser radiation unit 20 is an element which has a laser path along which a laser travels therein and which radiates a laser to the outside upon performing the treatment in the state in which the laser radiation unit 20 has been connected to the cable 13.

As described above, a laser generated by the main body 10 is transferred to the laser radiation unit 20 along the optical fiber of the cable, and controlled through the manipulation of the control panel 11 of the main body 10 or the laser radiation unit 20. Accordingly, a laser for the treatment or test of the human body can be radiated.

FIGS. 2 and 3 are schematic diagrams shown based on the element that belongs to the elements of the laser apparatus of FIG. 1 and that generates a laser. The configuration of the laser apparatus according to the present embodiment is described in more detail below with reference to FIGS. 2 and 3.

In accordance with one embodiment given with reference to FIG. 2, the laser radiation unit 20 may be equipped with the pumping laser supply unit 200 generating a pumping laser L2 and the laser output unit 100 capable of radiating an output laser L1 to a human body tissue using the pumping laser L2.

If the pumping laser supply unit 200 is disposed within the laser radiation unit 20 as in FIG. 2, the pumping laser supply unit 200 is disposed in parallel to the laser output unit 100, so the emitted pumping laser L2 can be directly supplied to the laser output unit 100.

The pumping laser supply unit 200 may emit the pumping laser L2 having a nano-second pulse width. That is, the present invention can provide the laser apparatus 1 having a high-speed pulse width. For example, the laser apparatus 1 can radiate a laser of a specific wavelength having a pulse width of several tens of ns to several hundreds of ns. Specifically, a laser having a pulse width of about 1 ns to 500 ns can be used. The laser of a nano-second pulse width output by the pumping laser supply unit 200 may be supplied to the laser output unit 100.

The laser output unit 100 is disposed within the laser radiation unit 20, and may generate the output laser L1 pumped by the pumping laser L2 to have a nano-second pulse width corresponding to the pulse width of the pumping laser L2. Accordingly, a laser itself incident on a specific medium of the laser output unit 100 has a nano-second pulse width. Accordingly, a laser output by the laser output unit 100 can be easily output as a laser having a nano-second pulse width.

In particular, if it is difficult to configure the medium 103 itself of the laser output unit 100 so that the medium outputs a laser having a nano-second pulse width, a laser of a nano-second pulse width can be easily configured using a separate pumping laser as in the present embodiment. In this case, it may be difficult to configure a shot pulse laser as the wavelength of a laser increases. In the present embodiment, the wavelength of an output laser may be longer than the wavelength of a pumping laser, and the pumping laser may have a wavelength capable of relatively easily configuring a laser of a nano-second pulse width.

Furthermore, as shown in FIG. 2, the laser radiation unit 20 may include a radiation unit end 21 detachably provided on one side from which the output laser L1 is radiated.

Furthermore, the laser output unit 100 is disposed within the radiation unit end 21 so that the radiation unit end 21 is detached, thereby being capable of easily replacing the laser output unit 100. Accordingly, treatment or a test can be performed using lasers of various wavelengths by replacing the laser output unit 100 that generates different output lasers L1, if necessary in use.

Specifically, the laser output unit 100 may include the output laser medium 103 capable of absorbing the pumping laser L2 and generating the output laser L1 having a wavelength different from that of the pumping laser L2.

A first total reflection mirror 106 and a first output mirror 107 may be provided on both sides of the output laser medium 103. The first total reflection mirror 106 is disposed on one side of the output laser medium 103, and it may transmit the pumping laser L2 toward the output laser medium 103 and reflect the output laser L1 oscillated by the output laser medium 103. The first output mirror 107 is disposed on the other side of the output laser medium 103 opposite the first total reflection mirror 106, and may partially reflect or transmit the output laser L1 oscillated by the output laser medium 103.

As described above, the period in which the output laser resonates has been configured using the first total reflection mirror 106 and the first output mirror 107, but the resonance period may be configured by coating both sides or one side of the output laser medium 103 with a reflective material (hereinafter, in FIGS. 5 and 6, a reflection mirror and output mirror for forming a resonant path may also be configured by coating both sides or one side of a medium with a reflective material).

Furthermore, the laser output unit 100 may further include a filter unit 105 that reflects the pumping laser L2 of lasers passing through the output laser medium 103 and the first total reflection and first output mirrors 106 and 107 and that transmits only the output laser L1. Furthermore, by way of example, the laser output unit 100 may be configured to include various optical elements, such as a condensing lens and a shutter for condensing a laser passing through the filter unit 105.

FIG. 3 shows an embodiment different from the embodiment shown in FIG. 2. In accordance with another embodiment given with reference to FIG. 3, the main body 10 may be equipped with the pumping laser supply unit 200 capable of emitting the pumping laser L2, and the laser radiation unit 20 may be equipped with the laser output unit 100 capable of radiating the output laser L1 to the skin using the pumping laser L2.

If the pumping laser supply unit 200 is disposed within the main body 10, it may be connected to the laser output unit 100 disposed in the laser radiation unit 20 through the cable 13. That is, the pumping laser L2 emitted by the pumping laser supply unit 200 may be supplied to the laser output unit 100 through the optical fiber of the cable 13.

Meanwhile, the laser output unit 100 is disposed within the laser radiation unit 20, and may generate the output laser L1 pumped by the pumping laser L2 to have a nano-second pulse width corresponding to the pulse width of the pumping laser L2. The detailed contents of the laser output unit 100 have been described in the one embodiment, and thus a detailed description thereof is omitted hereinafter.

An effect generated upon treating a human skin tissue due to the output laser L1 output by the laser output unit 100 and a wavelength laser absorbed by the laser output unit 100 with high efficiency are described below.

Referring back to FIGS. 2 and 3, as described above, the laser output unit 100 includes the output laser medium 103 absorbing the pumping laser L2 and generating the output laser L1 having a wavelength different from that of the pumping laser L2.

In this case, the wavelength of the pumping laser L2 may be 650 nm, and the wavelength of the output laser L1 generated by the output laser medium 103 may be 2940 nm. Such an output laser medium 103 may include Er:YAG.

Water and collagen form the greater part of chromophore, that is, a skin tissue component that absorbs a laser or light, such as ultraviolet rays. In this case, the major absorption peak of water lies in 2940 nm (the wavelength of the Er:YAG laser) and 10.6 um (the wavelength of a CO2 laser). A wavelength in which a laser or light is most absorbed is a 2940 nm region. If a laser having the wavelength of the 2940 nm band is radiated to the skin and penetrates into the skin in depth of several um, there is an advantage in that thermal damage is rarely generated other than a tissue to which the laser has been radiated. Accordingly, treatment, such as the decortication of the skin, can be precisely performed without damage to a neighbor tissue using such a laser. There may be an excellent effect in treatments for solar lentigo, that is, a pigmented lesion on a surface of the epithelium, and a scar.

Accordingly, the laser apparatus according to the present embodiment 1 configures the output laser medium 103 using Er:YAG, and it may be configured to radiate an output laser of a 2940 nm wavelength to the skin. In this case, the configuration using Er:YAG as the output laser medium 103 is one example, and the laser apparatus may be configured using various laser media.

Meanwhile, if Er:YAG is used as the output laser medium 103, the pumping laser L2 may be configured using an Er:YAG laser having a wavelength of an excellent absorption characteristic so that the output laser medium can be effectively pumped.

Figure 4:
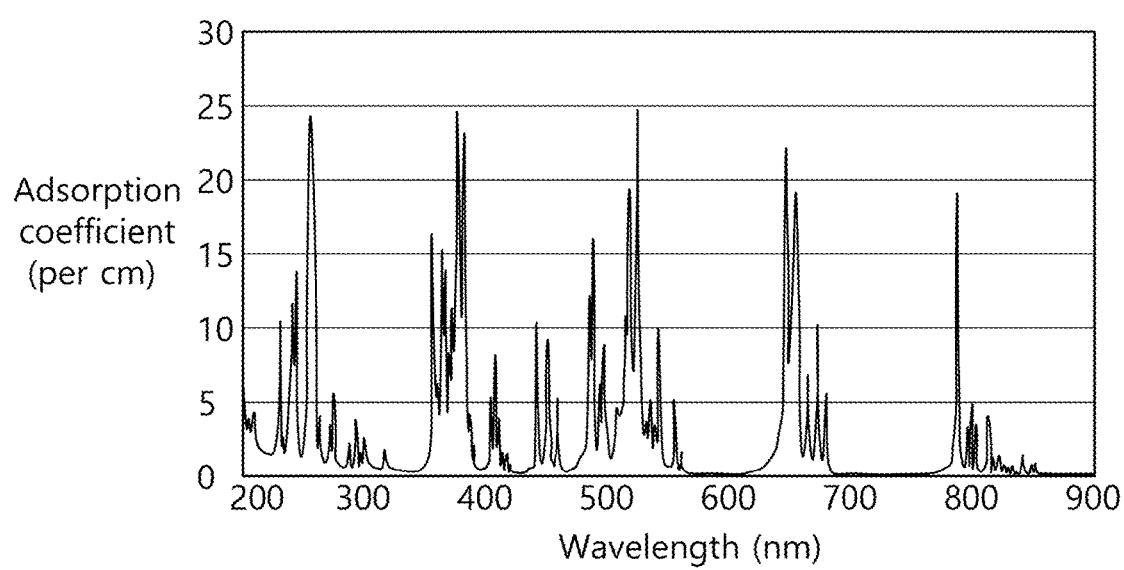
FIG. 4 is a graph showing the wavelength characteristics of a pumping laser absorbed by the Er:YAG of a laser output unit of FIGS. 2 and 3.

FIG. 4 is a graph showing the absorption characteristic of Er:YAG according to a wavelength. From the graph of FIG. 4, it may be seen that the Er:YAG has a high absorption characteristic with respect to light of a specific wavelength region. FIG. 4 shows that the Er:YAG has a high absorption characteristic in 250~280 nm, 350~380 nm, 520~550 nm, 630~670 nm and 780~820 nm. Accordingly, the laser apparatus of the present embodiment can pump the output laser medium using a laser of a wavelength having a high absorption characteristic as a pumping laser. By way of example, in the present embodiment, a laser having a wavelength of 630~670 nm is used as the pumping laser L2, and the output laser of 2940 nm is generated using the pumping laser L2.

Figure 5:
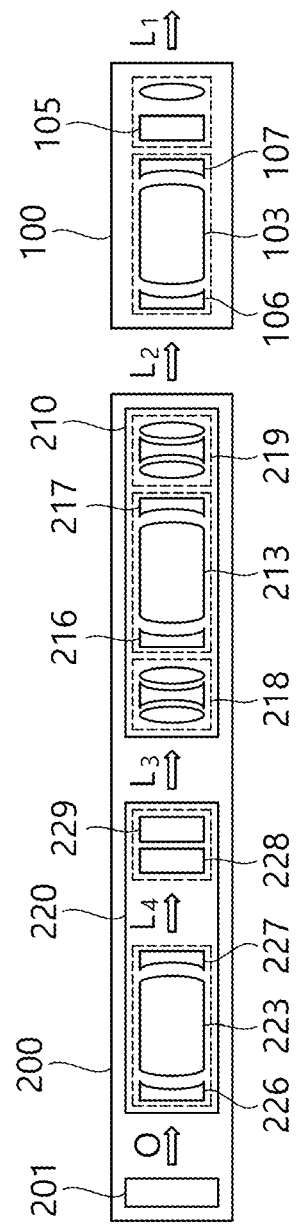
FIG. 5 is a schematic diagram showing a laser apparatus according to another embodiment of the present invention.

FIG. 5 is a schematic diagram showing a laser apparatus according to another embodiment of the present invention.

As in the aforementioned embodiment, the laser apparatus 1 according to the present embodiment is also configured to include a main body 10, a laser radiation unit 20, a pumping laser supply unit 200 and a laser output unit 100. Unlike in the aforementioned embodiment, in the laser apparatus 1 according to the present embodiment, the pumping laser supply unit 200 may be configured to include a laser oscillation unit 220 and a dye laser source 210.

The main body 10, the laser radiation unit 20 and the laser output unit 100 have been described in the previous embodiment and a detailed description thereof is omitted. The elements of the pumping laser supply unit 200 are chiefly described in detail. The pumping laser supply unit 200 is configured to include a light source 201, the laser oscillation unit 220 and the dye laser source 210.

The laser oscillation unit 220 may include the light source 201, such as a flash lamp disposed within the main body 10 and emitting light by power supplied by a power supply unit, and a laser medium 223 for oscillation absorbing excited light O received from the light source 201 and generating a supply laser L4 or oscillation laser L3.

Furthermore, the laser oscillation unit 220 may include a third total reflection mirror 226 and third output mirror 227 disposed on both sides of the laser medium 223 for oscillation and amplifying a laser by totally reflecting and partially reflecting light output by the laser medium 223 for oscillation, respectively. Thereafter, the laser oscillation unit 220 may emit the sufficiently amplified oscillation laser L3 or supply laser L4.

By way of example, the laser medium 223 for oscillation according to the present embodiment may include Nd:YAG that outputs the nano-second supply laser L4 having a wavelength of 1064 nm.

Furthermore, the laser oscillation unit 220 may optionally include KTP crystals 228 and a KTP mirror 229. The KTP crystals 228 and the KTP mirror 229 are elements which are disposed on one side of the laser medium 223 for oscillation and to which the supply laser L4 is incident and from which the oscillation laser L3 having a wavelength different from that of the supply laser is output. In this case, the KTP crystals 228 convert some of or the entire incident supply laser L4 into the supply laser L4 having a different wavelength. The KTP mirror 229 is provided at the back of the KTP crystals 228 and configured to transmit a wavelength corresponding to the oscillation laser L3 and to reflect a wavelength corresponding to the supply laser L4.

For example, when a laser having a wavelength of 1064 nm is incident, the KTP crystals 228 convert some of the laser into a laser having a wavelength of 532 nm. The converted laser of the 1064 nm wavelength passes through the KTP mirror 229, and the not-converted laser of the 532 nm wavelength is reflected by the KTP mirror 229. The front (the direction in which the oscillation laser is incident) of the KTP mirror 229 has been coated to totally reflect the laser of the 1064 nm wavelength and to transmit the laser of the 532 nm wavelength. The back (the direction in which the supply laser is output) of the KTP mirror 229 has been coated to transmit only a laser corresponding to the laser of the 532 nm wavelength.

Accordingly, the laser oscillation unit 220 according to the present embodiment can optionally generate the oscillation laser L3 having the wavelength of 1064 nm or 532 nm. In the present embodiment, Nd:YAG has been used as the laser medium for oscillation, but this is only an example and the laser medium for oscillation may be configured using various media.

Thereafter, the dye laser source 210 may absorb the oscillation laser L3 output by the laser oscillation unit 220 and emit a pumping laser L2 having a nano-second pulse width.

The dye laser source 210 is included within the pumping laser supply unit 200. Like the aforementioned pumping laser supply unit 200, the dye laser source 210 may be disposed within the main body 10 or may be disposed within the laser radiation unit 20 (refer to FIGS. 2 and 3).

If the dye laser source 210 is disposed within the laser radiation unit 20, it is disposed in parallel to the laser output unit 100 and can directly supply the emitted pumping laser L2 to the laser output unit 100. If the dye laser source 210 is disposed within the main body 10, it may be connected to the laser output unit 100 disposed in the laser radiation unit 20 through the cable 13. The pumping laser L2 emitted by the pumping laser supply unit 200 may be supplied to the laser output unit 100 through the optical fiber of the cable 13.

The dye laser source 210 may use a solid laser dye 213 as a medium so that it can generate a dye laser. In the present embodiment, the laser dye 213 capable of generating light of a 650 nm wavelength may be used.

Furthermore, the dye laser source 210 may include a second total reflection mirror 216 and second output mirror 217 on both sides of the solid laser dye 213 disposed within the dye laser source 210. The second total reflection mirror 216 is spaced apart from the solid laser dye 213 on one surface of the solid laser dye 213, and the second output mirror 217 is disposed opposite the second total reflection mirror 216 on the other surface of the solid laser dye 213. In this case, if pumping light (the supply laser) supplied to the dye laser source 210 is 532 nm, the second total reflection mirror 216 is configured to transmit the 532 nm light toward the solid laser dye 213 and to reflect light of 585 nm and 650 nm. Furthermore, the second output mirror 217 is configured to reflect the 532 nm light and to reflect part of the 585 nm and 650 nm light and transmit part of the 585 nm and 650 nm light. Accordingly, the pumping laser L2 output by the dye laser source 210 may be 585 nm or 650 nm. In the present embodiment, light of 650 nm having a nano-second pulse width is used.

Thereafter, the nano-second pumping laser L2 having the wavelength of 650 nm, output by the pumping laser supply unit 200, may be transferred to the laser output unit 100.

In this case, the example illustrates the laser dye 213 capable of generating the light of a 650 nm wavelength, but the solid laser dye 213 may be configured using a variety of types of laser dyes in addition to the laser dye.

Furthermore, the dye laser source 210 may include a first optical element unit 218 and a second optical element unit 219. In this case, the first optical element unit 218 is disposed on the path of externally incident light, and makes incident the laser on the laser dye 213. Furthermore, the second optical element unit 219 is disposed opposite the first optical element unit 218 on one side of the laser dye 213, and forms the path from the laser oscillation unit 220 to the pumping laser L2. Each of the first optical element unit 218 and second optical element unit 219 may be configured to include at least one optical element, such as a plurality of lenses, a filter and a shutter.

Accordingly, the laser oscillation unit 220 and the dye laser source 210 can supply the laser output unit 100 with a laser of a wavelength having a high absorption band with respect to the medium of the laser output unit 100 while having a nano-second pulse width through the above construction. Effective treatment and test can be performed as described above by radiating a laser whose wavelength has been converted into the output laser L1 to a local area of a patient who requires a surgical procedure.

Figure 6:
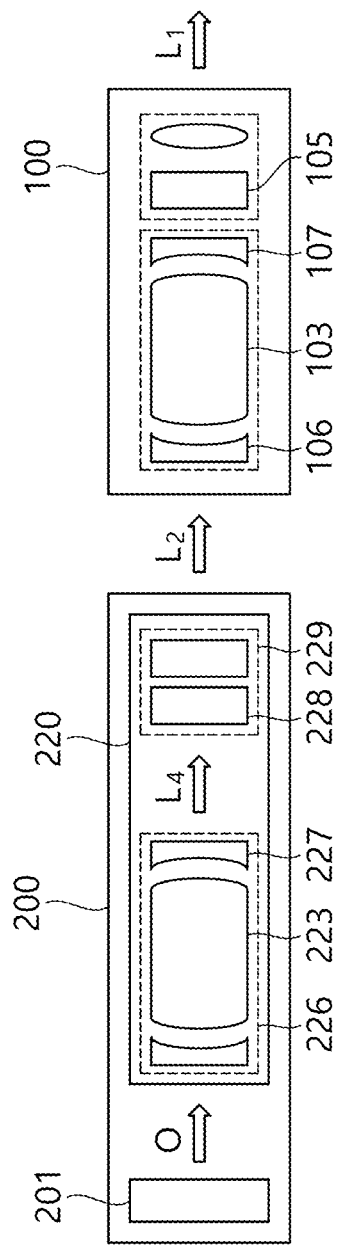
FIG. 6 is a schematic diagram showing a laser apparatus according to yet another embodiment of the present invention.

FIG. 6 is a schematic diagram showing a laser apparatus according to yet another embodiment of the present invention. As in the aforementioned embodiment, in the embodiment shown in FIG. 6, the laser apparatus 1 is configured to include a main body 10, a laser radiation unit 20, a pumping laser supply unit 200 and a laser output unit 100.

However, the laser apparatus 1 according to an embodiment of the present invention may be configured so that a laser oscillation unit 220 disposed in the pumping laser supply unit 200 emits a pumping laser L2 and the emitted pumping laser L2 is directly supplied to the laser output unit 100.

The laser oscillation unit 220 may include a light source 201, such as a flash lamp disposed within the main body 10 to emit light by power supplied by a power supply unit, and a laser medium 223 for oscillation that absorbs light O received from the light source 201 and generates the pumping laser L2.

Furthermore, the laser oscillation unit 220 may include a third total reflection mirror 226 and third output mirror 227 disposed on both side of the laser medium 223 for oscillation and amplifying a laser by totally reflecting and partially reflecting the light output by the laser medium 223, respectively. Thereafter, the laser oscillation unit 220 can emit the sufficiently amplified pumping laser L2.

In this case, the pumping laser L2 output by the laser oscillation unit 220 and having a nano-second pulse width may be supplied to the laser output unit 100.

The laser output unit 100 is disposed within the laser radiation unit 20, and may generate an output laser L1 pumped by the pumping laser L2 to have a nano-second pulse width corresponding to the pulse width of the pumping laser L2. Accordingly, a laser itself incident on a specific medium of the laser output unit 100 has a nano-second pulse width, so a laser subsequently output by the laser output unit 201 can be easily output as a laser having a nano-second pulse width. In this case, there is an effect in that a laser of a high wavelength having a nano-second pulse width that was difficult to implement conventionally can be easily implemented.

The detailed configurations of the laser oscillation unit 220 and the laser output unit 100 have been described in the previous embodiment, and thus a detailed description thereof is omitted.

Figure 7:
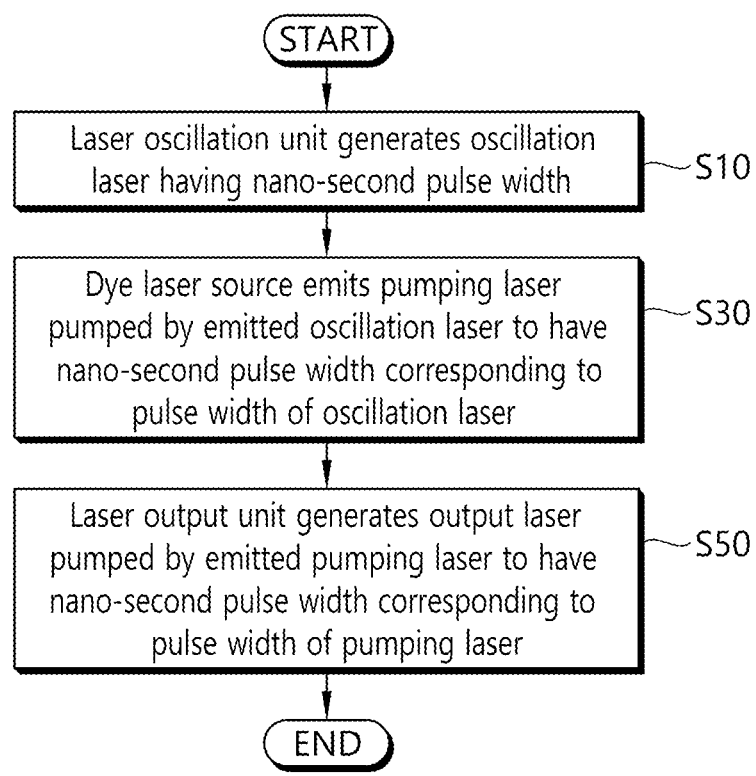
FIG. 7 is a flowchart showing a method of driving the laser apparatus according to an embodiment of the present invention.

FIG. 7 is a flowchart showing a method of driving the laser apparatus according to an embodiment of the present invention.

As shown in FIG. 7, the method of driving the laser apparatus according to the embodiments of the present invention is described below.

First, the laser oscillation unit 220 generates an oscillation laser having a nano-second pulse width (S10). Specifically, the laser oscillation unit 220 may absorb the light O from the light source 201 that emits light by power supplied thereto, and may generate a supply laser L4 having a nano-second pulse width.

In this case, the laser oscillation unit 220 may amplify a laser by totally reflecting and partially reflecting the light, output by the laser medium 223 for oscillation, respectively, through the third total reflection mirror 226 and third output mirror 227 disposed on both sides of the laser medium 223 for oscillation. Thereafter, the laser oscillation unit 220 can emit the sufficiently amplified supply laser L4.

In accordance with one embodiment, the laser medium 223 for oscillation may include Nd:YAG capable of outputting the supply laser L4 of a 1064 nm wavelength.

Thereafter, the laser of the 1064 nm wavelength generated by the Nd:YAG medium may generate the oscillation laser L3 through the KTP crystals 228 and the KTP mirror 229. The wavelength of the oscillation laser L3 converted through the KTP crystals 228 and the KTP mirror 229 may be 532 nm.

Thereafter, the oscillation laser L3 having a nano-second pulse width travels to the dye laser source 210.

Furthermore, the dye laser source 210 using the laser dye as the medium may absorb the oscillation laser L3 and generate the pumping laser L2 (S30).

As described above, if the pumping laser supplied from the laser oscillation unit 220 to the dye laser source 210 is 532 nm, the pumping laser L2 of the 585 nm or 650 nm wavelength may be generated by the second total reflection mirror 216 and the second output mirror 217. The generation of the pumping laser L2 has been described in detail above and thus the description thereof is omitted. One embodiment of the present invention illustrates that the laser dye 213 capable of generating light (pumping laser L2) of a 650 nm wavelength having a nano-second pulse width is used.

Thereafter, the pumping laser L2 having the nano-second pulse width travels to the laser output unit 100.

The laser output unit 100 may output the output laser L1 pumped by the pumping laser L2 to have a nano-second pulse width corresponding to the pulse width of the pumping laser L2 (S50).

Furthermore, the laser output unit 100 may include the output laser medium 103 capable of absorbing the pumping laser L2 and converting the absorbed laser into the output laser L1 having a wavelength different from that of the pumping laser L2. In accordance with one embodiment, the output laser medium 103 may include Er:YAG.

For example, the laser output unit 100 including Er:YAG may convert the nano-second pumping laser L2 having the proposed 650 nm wavelength into the nano-second output laser L1 having a 2940 nm wavelength. That is, as described above, if the pumping laser L1 supplied from the dye laser source 210 to the laser output unit 100 is 650 nm, the pumping laser L1 having the 2940 nm wavelength, amplified by the first total reflection mirror 106 and the first output mirror 107 disposed on both sides of the output laser medium 103, may be generated.

Thereafter, the pumping laser L1 is provided as energy necessary for each lesion, thus being capable of improving a treatment effect.

In this case, the laser having the 2940 nm wavelength has a skin penetration depth of several um because it has the greatest absorbance for water, and thus rarely gives thermal damage to a tissue other than a tissue to which the laser has been radiated. Accordingly, if treatment, such as skin decortication, is performed using the laser apparatus 1 according to the present invention, treatment such as ultrafine decortication can be performed without thermal damage to a surrounding tissue. In this case, there may be an excellent effect in treatments for solar lentigo, that is, a pigmented lesion on a surface of the epithelium, and a scar.

Furthermore, the expansion of a new treatment area can be expected because the laser apparatus can easily implement a laser having sufficient energy and having a 2940 nm wavelength of a nano-second pulse width that was commercially impossible.

Although the embodiments of the present invention have been described above with reference to the accompanying drawings, a person having ordinary skill in the art to which the present invention pertains will understand that the present invention may be implemented in other detailed forms without changing the technological spirit or essential characteristics of the present invention. Therefore, it should be understood that the aforementioned embodiments are illustrative from all aspects and are not limitative. The scope of the present invention is defined by the appended claims rather than the detailed description, and the meaning and scope of the appended claims and all changes or modified forms derived from equivalents thereof should be construed as being included in the scope of the present invention.

The invention claimed is:
1. A laser apparatus, comprising:
   a pumping laser supply unit emitting a pumping laser having a nano-second pulse width; and
   a laser output unit disposed on one side of the pumping laser supply unit and generating an output laser pumped by the pumping laser to have a nano-second pulse width corresponding to the pulse width of the pumping laser, wherein the laser output unit comprises an output laser medium that comprises Er:YAG and the pumping laser supplied to the laser output unit has a wavelength of 630-670 nm.

2. The laser apparatus of claim 1, wherein the output laser medium absorbs the pumping laser and generates the output laser having a wavelength different from a wavelength of the pumping laser.

3. The laser apparatus of claim 2, wherein the laser output unit further comprises:
   a total reflection mirror disposed on one side of the output laser medium, transmitting the pumping laser toward the output laser medium, and reflecting the output laser oscillated by the output laser medium; and
   an output mirror disposed opposite the total reflection mirror on the other side of the output laser medium and partially reflecting or transmitting the output laser oscillated by the output laser medium.

4. The laser apparatus of claim 2, wherein the output laser emitted by the laser output unit has a wavelength of 2940 nm.

5. The laser apparatus of claim 1, wherein the pumping laser supply unit comprises a dye laser source generating the pumping laser.

6. The laser apparatus of claim 5, wherein:
   the pumping laser supply unit further comprises a laser oscillation unit configured to emit an oscillation laser having a nano-second pulse width, and
   the dye laser source generates the pumping laser amplified by the oscillation laser emitted by the laser oscillation unit.

7. The laser apparatus of claim 6, wherein:
   the laser oscillation unit comprises a laser medium for oscillation absorbing externally incident light and outputting the oscillation laser, and
   the laser medium for oscillation comprises Nd:YAG.

8. The laser apparatus of claim 6, wherein the oscillation laser has a 532 nm wavelength.

9. The laser apparatus of claim 1, further comprising a filter unit disposed within the laser output unit, reflecting the pumping laser and transmitting the output laser.

10. A method of driving a laser apparatus, the method comprising steps of:
    emitting a pumping laser having a nano-second pulse width by a pumping laser supply unit; and
    generating an output laser pumped by the pumping laser, the output laser having a nano-second pulse width corresponding to the pulse width of the pumping laser,
    wherein the output laser is generated by a laser output unit, the laser output unit comprising an output laser medium that comprises Er:YAG, and the pumping laser supplied to the laser output unit has a wavelength of 630-670 nm.

11. The method of claim 10, wherein the step of emitting the pumping laser having the nano-second pulse width comprises a step of generating, by a dye laser source using a laser dye as a medium, the pumping laser.

12. The method of claim 11, further comprising a step of emitting, by a laser oscillation unit, an oscillation laser having a nano-second pulse width prior to the step of generating, by the dye laser source, the pumping laser,
    wherein the dye laser source generates the pumping laser amplified by the oscillation laser emitted by the laser oscillation unit.

13. The method of claim 12, wherein the output laser, the pumping laser, and the oscillation laser have respective nano-second pulse widths and wavelengths of 2940 nm, 650 nm, and 532 nm, respectively.

14. The method of claim 12, wherein the laser oscillation unit includes a medium comprising Nd:YAG.

15. The method of claim 10, wherein the output laser medium absorbs the pumping laser and generates the output laser having a wavelength different from a wavelength of the pumping laser.

* * * * *